United States Patent [19]

Baker

[11] Patent Number: 4,919,939

[45] Date of Patent: Apr. 24, 1990

[54] PERIODONTAL DISEASE TREATMENT SYSTEM

[75] Inventor: Richard W. Baker, Palo Alto, Calif.

[73] Assignee: Pharmetrix Corporation, Menlo Park, Calif.

[21] Appl. No.: 216,802

[22] Filed: Jul. 8, 1988

Related U.S. Application Data

[63] Continuation-in-part of Ser. No. 856,961, Apr. 29, 1986, Pat. No. 4,780,320.

[51] Int. Cl.$^5$ ............................................. A61L 15/03

[52] U.S. Cl. ................................... 424/493; 424/486; 424/497

[58] Field of Search ............... 424/493, 489, 484, 490, 424/486, 497

Primary Examiner—Nancy A. B. Swisher
Attorney, Agent, or Firm—A. J. Castro; J. Farrant

[57] ABSTRACT

A controlled release drug delivery system for placement in the periodontal pocket, gingival sulcus, tooth socket, wound or other cavity within the mouth. The system incorporates drug-containing microparticles in a fluid carrier medium, and is effective in the environment of use for up to 30 days.

47 Claims, 3 Drawing Sheets

PERIODONTAL DISEASE TREATMENT SYSTEM

CROSS REFERENCE TO RELATED APPLICATIONS

This application is a continuation-in-part of U.S. patent application Ser. No. 856,961, filed April 29, 1986 now U.S. Pat. No. 4,780,320.

FIELD OF THE INVENTION

This invention relates to a controlled release drug delivery system for use in the mouth, and particularly to systems for placement in the periodontal pocket to treat periodontal disease.

BACKGROUND OF THE INVENTION

Periodontal disease, with caries, is the most important cause of loss of teeth. It is well established that bacteria are directly involved in both the onset and progression of periodontal disease. See for example J. Slots, "Subgingival Microflora and Periodontal Disease," *J. Clin. Periodontal.* 6, 315 (1979) and S. S. Socransky, "Microbiology of Periodontal Disease—Present Status and Future Considerations," *J. Periodontol.* 48, 497 (1977). This has led to the widespread use of antibiotics in the treatment of periodontal disease, and particularly to the use of tetracycline, since significantly higher levels of tetracycline are found in gingival fluid than in blood after administration of single or multiple oral doses. (J. M. Gordon et al., "Sensitive Assay for Measuring Tetracycline Levels in Gingival Crevice Fluid," *Antimicrob. Agents Chemother.* 17, 193 (1980), J. M. Gordon et al., "Concentrations of Tetracycline in Human Gingival Fluid after Single Doses," *J. Clin. Peridontol.* 8, 117 (1981) and J. M. Gordon et al., "Tetracycline: Levels Achievable in Gingival Crevice Fluid and in vitro Effect on Subgingival Organisms. Part 1. Concentrations in Crevicular Fluid after Repeated Doses," *J. Periodontol.* 52, 609 (1981).) However, the typical effective tetracycline oral dose of one gram per day for 30 days can lead to serious side effects. It has been estimated that the dose should be of the order of one hundred times smaller to avoid these effects. A more satisfactory approach then is to administer the antibiotic topically using a controlled release device to sustain an effective dose for the required length of time. Because the drug is delivered locally, a much reduced dose will suffice for effective therapy, and harmful side effects can be reduced or eliminated.

Long lasting drug delivery systems presently used in the oral cavity fall broadly into two groups; either troches, pastilles or tablets which adhere to the oral mucosa in some way, or drug containing strips or dosage forms which are attached to the gums, teeth or other interior surface of the mouth. A good example of the former category is U.S. Pat. No. 4,039,653. This patent discloses a sustained release tablet coated with a pharmaceutically acceptable oral adhesive, which is placed in an upper corner of the mouth and is capable of dispensing an odor-masking agent, local anaesthetic or other medication in a sustained fashion for periods of up to twelve hours. U.S. Pat. No. 4,250,163 discloses a method of administering a broad range of medications to the oral cavity by means of a water-swellable and mucosa-adhesive polymeric matrix, which can be in the form of a tablet, powder or granules and which is effective for times of the order of a few hours. As can be seen from these and other examples, such as U.S. Pat. Nos. 4,226,848, 4,369,172 and 4,059,686, such troches and tablets are normally effective for periods of hours rather than days, and a course of treatment lasting one month would require the use of numerous tablets. Furthermore they are inappropriate to the treatment of periodontal disease because the drug is released into the saliva or oral mucosa, and does not penetrate the periodontal pocket to any significant extent. Buccal tapes, strips and forms suffer from the same disadvantages. For example, the buccal dosage form disclosed in U.S. Pat. No. 3,972,995 was found to be effective without leaking, if not wrinkled or dislodged by the teeth, for about one hour only. This highlights another disadvantage of existing methods of dispensing drugs for oral therapy; they may slip or be dislodged by the tongue or teeth, may be uncomfortable to a greater or lesser degree, and may interfere with the normal oral functions to some extent. Recent developments in the art are directed toward delivering the therapeutic agent directly to the periodontal pocket, in some cases in a controlled release formulation. Gordon et al. have described the use of a drug-filled polymer hollow fiber. (J. M. Goodson et al., "Periodontal Therapy by Local Delivery of Tetracycline," *J. Clin. Periodontol.* 6, 83 (1979), J. Lindhe et al., "Local Tetracycline Delivery Using Hollow Fiber Devices in Periodontal Therapy," *J. Clin. Periodontol.* 6, 141 (1979) and R. L. Dunn et al., "Monolithic Fibers for Controlled Delivery of Tetracycline," in *Proc. Ninth Int. Symposium on Controlled Release of Bioactive Materials*, Ft. Lauderdale, Fl., July (1982).) This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman (J. Coventry and H. N. Newman, "Experimental Use of a Slow Release Device employing Chlorhexidine Gluconate in Areas of Acute Periodontal Inflammation," *J. Clin. Periodontol.* 9, 129 (1982)) and Addy et al. (M. Addy et al., "The Development and in vitro Evaluation of Acrylic Strips and Dialysis Tubing for Local Drug Delivery," *J. Periodontol.* 53, 693 (1982)) using acrylic strips 1 mm or more long, impregnated with chlorhexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538. Another strip, employing a water soluble polymer of a particular elasticity and viscosity, is disclosed by Suzuki et al. in U.S. Pat. No. 4,569,837. Although these devices may be able to dispense an appropriate drug for a time span of a week or more, they are inappropriate to widespread use because they are difficult and time consuming to apply and may be dislodged by the patient during normal oral functions.

U.S. patent application Ser. No. 856,961, copending with the present invention, provides a novel controlled release system that can deliver antibiotics or other drugs in the periodontal pocket for a prolonged period of time, without interfering in any way with normal oral functions.

The present invention provides for the controlled delivery of a range of agents that are efficacious in the treatment of periodontal disease and other gingival or oral problems.

SUMMARY OF THE INVENTION

This invention is a controlled release drug delivery system that can be placed in the periodontal pocket. The system is particularly useful in control and treatment of periodontal disease, but can also be used for controlled delivery at the affected site for post-operative pain, inflammation or bleeding, or for treatment of other local diseases of the oral cavity or systemic diseases with oral manifestations. The system offers a major advantage over systemic therapy, in that the useful therapeutic dose of many drugs is found to be one or two orders of magnitude less than the corresponding oral dose, thereby avoiding all or many of the side effects associated with long-term oral delivery of antibiotics, antiinflammatories, or other potent drugs. The system comprises microparticles or microcapsules, hereinafter referred to as microparticles, suspended in a pharmaceutically acceptable carrier medium. The microparticles are between 10 and 500 microns in size, and consist of an active agent dispersed within or encapsulated by a rate-controlling polymer matrix. This microparticle/carrier system is a major improvement over previously known controlled release systems for use in treating periodontal disease. Because of the fluid carrier medium, and the small microparticle size, the system can penetrate throughout deep, narrow or complex periodontal pockets. In comparison, solid strips, fibers or other comparatively large dosage forms are limited to placement in the region adjacent to the gingival margin, where the therapeutic effect is less, and where they are more susceptible to dislodgement.

Microparticles of this specification can be prepared by a variety of well-established techniques, for example solvent evaporation, coacervation or spray-drying. The active agent may be chosen from antiseptics, antibiotics, antiinflammatories, local anaesthetics, tissue growth promoters, and tissue destruction inhibitors, for example. The system may also be used to encapsulate simple prophylactic agents, such as calcium or fluoride ion. The polymer matrix may be chosen from a range of medically suitable materials and varied to provide the required release rate for the drug involved. The drug release mechanism may be by diffusion of the drug through the intact polymer, by gradual erosion of the polymer matrix, or by leaching of the agent from pores. Embodiments employing biodegradable polymers can limit the microparticle life and prevent prolonged microparticle entrapment in the periodontal pocket.

The carrier medium may be an aqueous solution, paste or gel. In general, the properties required are that it should be pharmaceutically acceptable (non-toxic and non-allergenic), promote good adhesion in the periodontal pocket, and have a high permeability for the active agent involved. A preferred embodiment of the invention employs a thermally gelling polymer such as Pluronic F127 from BASF Wyandotte. In aqueous solution this polymer is a free-flowing fluid at room temperature, but gels rapidly above 30° C. Embodiments of the invention are typically placed in the periodontal pocket or other desired site by means of a syringe and needle. The system may be tailored to release the desired agent for periods ranging from a few hours to many days.

It is an object of the invention is to provide a controlled release system to deliver a drug or other active agent to the periodontal pocket or other site within the oral cavity for prolonged periods.

It is another object of the invention to provide a controlled release drug delivery system that is self-retaining in the periodontal pocket.

It is another object of the invention to provide a controlled release drug delivery system that can penetrate throughout the periodontal pocket.

It is another object of the invention to provide a controlled release drug delivery system for the periodontal pocket or the oral cavity that does not interfere with normal oral functions, and is not easily dislodged by the patient.

It is another object of the invention to provide a controlled release drug delivery system for use in the periodontal pocket, gingival sulcus or other localized oral site, where the drug delivery is controlled by diffusion through the polymer matrix.

It is another object of the invention to provide a controlled release drug delivery system for use in the periodontal pocket, gingival sulcus or other localized oral site, where the drug delivery is controlled by erosion of the polymer matrix.

It is another object of the invention to provide a controlled release drug delivery system for use in the periodontal pocket, gingival sulcus or other localized oral site, where the drug delivery is controlled by leaching from pores within the matrix.

It is another object of the invention to provide a controlled release drug delivery system for dispensing antiseptics in the periodontal pocket, gingival sulcus or other localized oral site.

It is another object of the invention to provide a controlled release drug delivery system for dispensing antibiotics in the periodontal pocket, gingival sulcus or other localized oral site.

It is another object of the invention to provide a controlled release drug delivery system for dispensing anaesthetics in the periodontal pocket, gingival sulcus or other localized oral site.

It is another object of the invention to provide a controlled release drug delivery system for dispensing anti-inflammatory agents in the periodontal pocket, gingival sulcus or other localized oral site.

It is another object of the invention to provide a controlled release drug delivery system for dispensing tissue growth promoters in the periodontal pocket, gingival sulcus or other localized oral site.

It is another object of the invention to provide a controlled release drug delivery system for dispensing tissue destruction inhibitors in the periodontal pocket, gingival sulcus or other localized oral site.

It is another object of the invention to provide a controlled release drug delivery system for dispensing minerals in the periodontal pocket, gingival sulcus or other localized oral site.

Other objects and advantages of the present invention will be apparent from the following description.

DETAILED DESCRIPTION OF THE INVENTION

Figure 1:
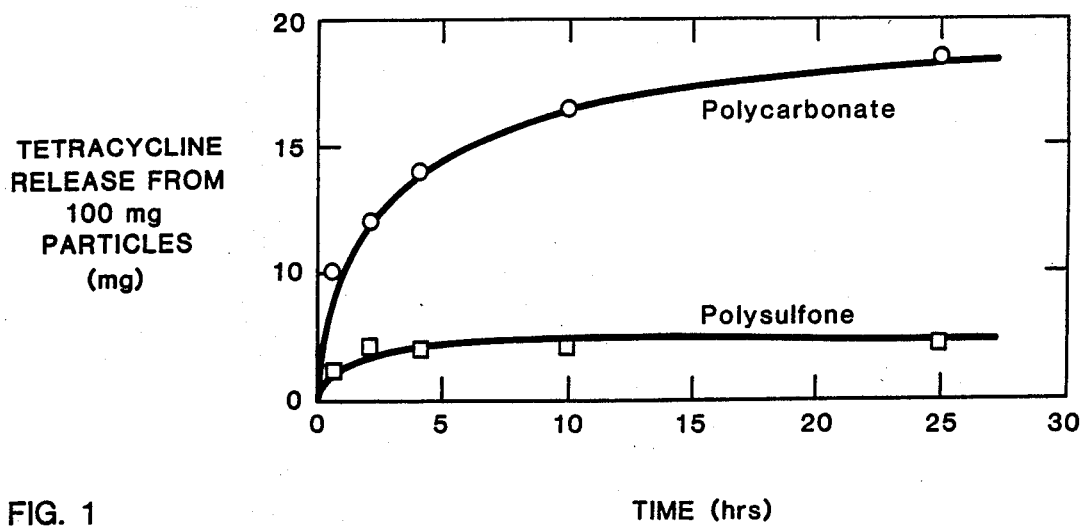
FIG. 1 is a graph of in vitro release of tetracycline free base from polysulfone and polycarbonate microparticles.

"Active agent" as used herein broadly includes any composition or compound of matter which when dispensed in the chosen environment of use produces a predetermined, beneficial and useful result.

"Drug" as used herein broadly includes physiologically or pharmacologically active substances for producing a localized effect at the administration site or a systemic effect at a site remote from the administration site.

Periodontal disease is a general term for a number of diseases that affect the periodontal tissue. These diseases are characterized by a range of symptoms including inflammation, bleeding, exudation of pus from the gingival sulcus, deepening of the sulcus to form periodontal pockets, tissue lesions, loss of connective tissue, alveolar bone loss, and ultimately tooth loosening and loss. The primary cause of periodontal disease is now believed to be bacterial infection of the plaque that forms on tooth surfaces below the gingival margin.

Current treatments for periodontal disease include professional cleaning to remove plaque and tartar, use of oral antiseptics, local or systemic antibiotic therapy, and various surgical procedures.

The system of the present invention is useful for prolonged, controlled dispensing of a range of drugs and agents used in connection with these types of treatment. Some examples are:

(a) Prophylactic prolonged application of minerals and ions, such as calcium or fluoride ion.

(b) Prolonged controlled exposure to local antiseptics. Preferred antiseptics for use in the present system include chlorhexidine and tibezonium iodide, an agent with activity similar to that of chlorhexidine, and effective in the presence of plaques, exudates, or variations in salivary pH.

(c) Controlled antibiotic therapy. The system of the present invention offers a major advantage over systemic antibiotic therapy in that effective dosages per tooth may be 100 times smaller or less than the corresponding oral dose. Thus the harmful side effects associated with long term antibiotic treatment are minimized or eliminated entirely. Preferred antibiotics for use in the system of the present invention include:

Aminoglycosides such as neomycin, gentamycin, kanamycin, tobramycin, netilmicin, sisomicin, amicamycin, their sulfates or other derivatives.

Macrolides such as erythromycin, its salts and other derivatives, spiramycin, josamicin or miocamicin.

Penicillins such as ampicillin, amoxicillin and the like.

Cephalosporins, for example, cefaclor, cefadroxil, cefazolin, cefoperazone, cefotaxime, cephalothin, cefalexin, ceforanide, cefonicide or ceftriaxone.

(d) Anaesthetic/analgesic delivery pre- or post surgery or to treat other mouth pain. Preferred agents include amide-type local anaesthetics such as lidocaine, mepivacaine, pyrrocaine, bupivacaine, prilocaine, etidocaine, or other widely used anaesthetics such as procaine.

(e) Local controlled delivery of non-steriodal anti-inflammatory drugs. As with antibiotics, relatively small doses, with correspondingly fewer side effects, are possible with the present invention. Particularly preferred drugs are ketorolac, naproxen, diclofenac sodium, and flurbiprofen.

Collagen is a fibrous protein found in connective tissue and bone matrix. Advanced periodontal disease is characterized by destruction of collagen, resulting in loss of connective tissue and bone. The activity of collagenase and other collagen-destructive enzymes has been shown to be responsible for this effect. There are, however, a number of agents available that possess activity against collagen-attacking proteases. For example, U.S. Pat. No. 4,735,945, incorporated herein by reference, describes the efficacy of sanguinarine and sanguinarine pseudoethanolate in inhibiting collagenase activity. Tetracyclines in general exhibit similar effects. European Patent Application No. 0,195,906, incorporated herein by reference, pages 20–22, discloses dedimethylaminotetracycline and other tetracyclines without antibiotic activity, that are useful as anti-collagenase agents. The present invention provides a novel controlled release system for delivering such anti collagen-destructive-enzyme agents.

It has also recently been shown that regrowth and repair of periodontal connective tissue can be encouraged with the aid of polypeptide mitogenic growth factors. See, for example, V. P. Terranova et al., "Biochemically Mediated Periodontal Regeneration", *J. Periodont. Res.*, 22, pages 248–251, incorporated herein by reference. The system of the present invention can be designed to encapsulate and release appropriate growth factors, including, but not limited to, epidermal growth factors (EGF), human platelet derived TGF-B, endothelial cell growth factors (ECGF), thymocyte-activating factors, e.g. fibroblast-derived TAF, platelet derived growth factors (PDGF), fibroblast growth factor (FGF), fibronectin or laminin.

The system comprises a plurality of microparticles or microcapsules between 10 and 500 microns in size, suspended in a pharmaceutically acceptable carrier. Microcapsules in this context are defined as reservoir systems in which a simple reservoir of active agent is surrounded by a membrane shell; microparticles are small monolithic entities in which the active agent is randomly dispersed through the particle matrix. Many practical formulations fall between these two definitions; for example microcapsules often agglomerate during the microencapsulation process, while the size of the active agent particles contained in a microparticle system is often of the same order as the size of the microparticles themselves. In the following discussion then, "microparticle" will be defined to mean microparticle, microcapsule or any intermediate form. Various physical and chemical methods for preparing microparticles have been developed over the past twenty years and the technology is well established and well documented. See for example Patrick B. Deasy, *Microencapsulation and Related Drug Processes*, Marcel Dekker Inc., New York, 1984. The more important methods are described below, and depending on the chemical and physical properties of the desired embodiment, any of these could be used to prepare the microparticles.

Coacervation was the first microencapsulation technique and remains one of the most widely used. Coacervation usually involves four steps. First a dispersion or emulsion of the active agent is prepared in an aqueous polymer solution. Secondly, the polymer is caused to precipitate slowly by some means: addition of a non-solvent, cooling, change of pH or ionic strength, or addition of an incompatible polymer solution for example. Under these conditions, most polymers initially precipitate as a highly swollen liquid polymer phase, this phenomenon being known as coacervation. During the precipitation, the liquid phase coats the dispersed active agent droplets. Finally the microparticles thus formed are separated from the solvent/non-solvent mixture, dried and sieved into different size fractions. Most industrial coacervation processes use aqueous solutions of gelatin and other water soluble polymers and can only encapsulate hydrophobic, water insoluble agents dissolved in an organic solvent. However the process can be inverted by using organic-solvent-soluble polymers with organic-solvent-insoluble active agents dissolved in an aqueous solution. Since many drugs are at least moderately water soluble, this makes the process appropriate to the preparation of microencapsulated pharmaceuticals. For example ethylcellulose has been used to prepare microparticles containing aspirin, indomethacin, paracetamol, theophylline and vitamins among others. The main disadvantage of the coacervation technique is that it requires considerable skill to produce particles with consistent properties, since the particle sizes and wall thickness may vary widely.

Interfacial polymerization occurs when two reactive monomers, each in different immiscible liquids, are brought into contact. The monomers are able to react only at the interface of the two solutions, where a polymer film forms. When one solution is dispersed in the other, the polymer film formed encapsulates the disperse phase. This process is not widely used for the commercial preparation of pharmaceuticals because of various practical problems; toxicity of remaining unreacted monomer, drug degradation as a result of reaction with the monomer, high permeability of the encapsulating polymer to the active agent involved, fragility of the capsules produced and non-biodegradability of the particles amongst others. However extensive research work has been done on the coating of high-molecular-weight biological materials such as enzymes with polyamides, and recently McGinity et al. have successfully encapsulated caffeine, sodium salicylate, theophylline and other drugs in a nylon coated particle by this technique. (J. W. McGinity et al., "Influences of matrices on nylon-encapsulated pharmaceuticals," *J. Pharm. Sci.* 70, 372–375 (1981).)

Solvent evaporation is another technique which is appropriate for the encapsulation of a water-soluble drug. First the polymer matrix material is dissolved in an organic solvent. Adding the active agent, dissolved in water, and emulsifying, produces a water-in-oil emulsion. This emulsion is re-emulsified in an aqueous solution, forming a water-in-oil-in-water emulsion. This final aqueous solution usually contains a polymer such as gelatin, to prevent aggregation. The solvent is then removed under reduced pressure to form a hard outer wall to the particles. Hydrophobic agents may also be prepared by solvent evaporation, but in this case the procedure is modified by first preparing an oil-in-water emulsion of the agent. This process has been used for example by Wakiyama et al. to prepare microparticles of butamben, tetracaine and dibucaine, where the polymer material used was polylactic acid in a solution of methylene chloride, methyl acetate or ethyl acetate. (N. Wakiyama et al., "Preparation and evaluation in vitro of polylactic acid microspheres containing local anaesthetics," *Chem. Pharm. Bull.* 29, 3363–68 (1981).) Recently Kojima et al. used the solvent evaporation technique to enclose various local anaesthetics in polycarbonate microspheres: sustained drug-release times measured in hundreds of hours resulted. (*Chem. Pharm. Bull.* 32, 2795–2802 (1982).)

Finally a number of simple physical techniques can be used to prepare microparticles, and spray drying, for example, is widely used in the preparation of food or pharmaceutical flavors. Spray dried particles are less satisfactory for preparing drugs however, as the particles tend to be non-uniform and the coating porous, causing the active agent to disperse too rapidly for a controlled-release application. However several penicillins have been microencapsulated in ethylcellulose in this way. See for instance U.S. Pat. No. 4,016,254 (April 1977).

The polymer matrix material chosen should be pharmaceutically acceptable, soluble in a variety of suitable solvents and available in different grades to enable the release rate of the active agent to be tailored as necessary. In general, biodegradable polymers, while not necessary, are preferred, because they avoid any potential problems associated with long-term entrapment of particles in the periodontal pocket. There are several mechanisms whereby the drug or agent can be released from the polymer material. These may be grouped into three broad categories: diffusion, erosion, and leaching. The aspects and advantages of each will now be discussed separately, although it should be appreciated that in an actual microparticle system, the drug release may frequently occur by a combination of two, or all three, of these mechanisms.

Diffusion-controlled systems operate by permeation of the substance to be released through the intact polymer to the surrounding environment. The system geometry may be either monolithic, with the agent to be released dispersed uniformly through the polymer matrix, or reservoir, with the agent surrounded by a shell of polymer material. In either case, the drug permeation rate through the polymer depends on the diffusion coefficient of the agent in the polymer, the solubility of the agent in the polymer, and the geometry of the system. A detailed discussion of the factors affecting diffusion coefficient and solubility, and their relationship to the molecular weight, molecular size, and drug melting point, is given in *Controlled Release of Biologically Active Agents*—R. W. Baker, John Wiley and Sons, 1987, Chapter 2, pages 22–36, incorporated herein by reference. As a general rule, diffusion-controlled release will be the preferred drug release mechanism for many standard drugs and agents, such as the antibiotics, anaesthetics, or antiseptics mentioned above. As shown in the Examples below, it is possible to tailor the drug/polymer combination and the device geometry to obtain the necessary therapeutic dose for the required time. Particularly preferred polymers for use in biodegradable diffusion-controlled systems are lactic-glycolic acid copolymers. These have an extensive history of use in medical applications, such as sutures and implants. They have also been used in other contexts to encapsulate drugs. For example, Setterstrom et al., *Polym. Mater. Sci. Eng.*, 53, 620–626 (1985) describes the use of ampicillin microencapsulated in poly(DL-lactide-co-glycolide) for topical application to wounds; effective levels of antibiotic are detectable at the wound site for at least fourteen days. Lactic-glycolic acid copolymers degrade into innocuous degradation products over periods of a few weeks. Copolymers with about equal percentages of lactic and glycolic degrade more rapidly than those that are primarily either lactic or glycolic acid. Other preferred biodegradable polymers that could be used in the system of the invention include polycaprolactones, polyorthoesters or polyacetals, all of which have been used as biodegradable matrices for drug delivery systems, or copolymers of these various materials. Embodiments incorporating non-biodegradable polymers can be prepared from a large number of polymers known in the art, including, but not limited to polycarbonate, polysulfone, polystyrene, polyurethane, polyamide, polyvinyl chloride, polyvinyl acetate, cellulose acetates, ethylcellulose, ethylene vinyl acetate, and various derivatives and copolymers of these.

In general, useful diffusion rates through the polymers listed above which typically have a maximum water sorption of 0 to 10 wt % is generally limited to drugs with molecular weights less than 200 to 300. For drugs above this molecular weight, for example some of the macrolides cephalosporins, penicillins and protein and polypeptide drugs, the rate of diffusion may be too low to be useful. In this case, microparticles made from highly hydrated and hydrophilic polymers can be used. These polymers typically sorb from 20 to 80 wt % water, and as a result, the rate of diffusion of even large molecules is relatively high. Hydroxy ethyl methacrylate and related polymers, polyacrylic acid copolymers, gelatin, starch, crosslinked polyvinyl alcohol, crosslinked polyamino acids and polyacrylicamide are all examples of this type of material.

The theory of drug release from solid microspheres was developed by Higuchi (T. Higuchi, J. Pharm. Sci. 52, 1145 (1963)). The release is controlled by the equation $$\frac{3}{2}\left(1-\left[1-\frac{M_t}{M_\infty}\right]^{\frac{2}{3}}-\frac{M_t}{M_\infty}\right)=\frac{3P\cdot t}{r_0^2 C_0}$$

$M_t/M_\infty$ is the fraction of total drug released after time t from a particle of radius $r_0$. The drug permeability in the matrix is P and the drug loading is $C_0$. This equation can be used to tailor the size of the microparticles, and the drug loading, so that the desired dosage level and release rate for the chosen embodiment is obtained.

Where polypeptides, or other large or unstable macromolecules or biological materials are to be dispensed, the molecule may be too large or too unstable to permeate by diffusion through the intact polymer phase. For delivering materials with high molecular weights, therefore, it may be necessary or preferable to deploy systems that operate by erosion control. Erosion-controlled systems normally have a monolithic geometry; in other words the active agent is uniformly dispersed within the polymer matrix. The agent does not diffuse through the polymer to any significant extent, and is thus essentially immobilized in the matrix until released by degradation of the surrounding material. Controlled release erosion-controlled systems are more difficult to design than diffusion-controlled systems; nevertheless they are useful where proteins or other large molecules are to be dispensed. Many biodegradable materials break down homogeneously by hydrolysis of labile bonds within the polymer; thus their release pattern is characterized by an initial time period where negligible amounts of drug are released, followed by a period where the drug release increases very rapidly as the matrix dissolves. This type of pattern represents a delayed, rather than a controlled, release system. To design a controlled release microparticle, capable of steady, slow release of agent, it is desirable, therefore, that the degradation of the particle occur as a surface phenomenon, so that the agent is released as progressive "shells" of the matrix are eroded away. Preferred polymers suitable for use in the system of the present invention will be those that break down by a surface degradation mechanism, for example certain polyanhydrides and polyacids. The polyanhydrides erode by a two-step process, thus:

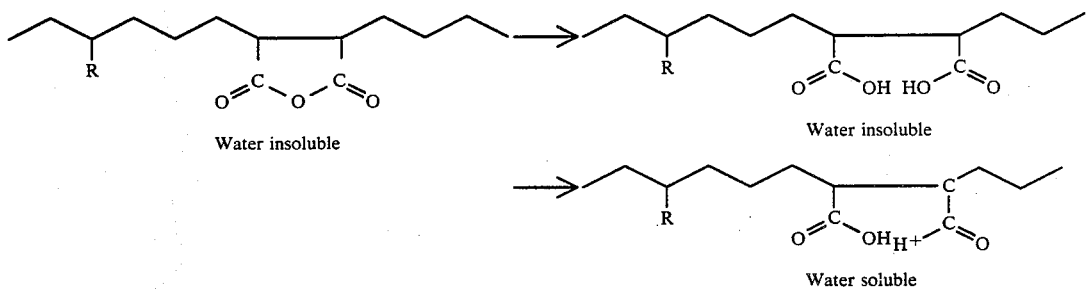

Water insoluble → Water insoluble

→ Water soluble

The polyacids dissolve according to the mechanism:

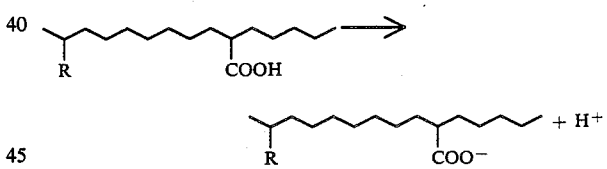

the rate of dissolution being dependent on the pH of the surrounding environment. Particularly preferred are acids or anhydrides based on maleic anhydride/methyl vinyl ester copolymers. The anhydrides can be converted into half esters of varying hydrophilicity by ring opening with an appropriate alcohol, as follows:

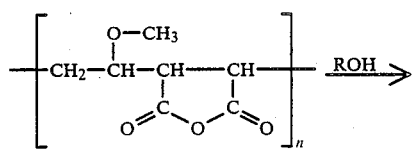

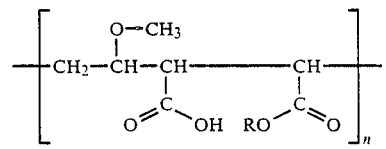

where R represents —$CH_3$, —$C_2H_5$, —$C_3H_8$, and so on.

Polymers of this type have been used as matrices for biodegradable drug dispersions, because their surface erosion characteristics lead to good constant release rates. (See, for example, J. Heller et al., "Controlled Drug Release by Polymer Dissolution. I. Partial esters of Maleic Anhydride Copolymers: Properties and Theory", *J. App Polym. Sci.*, 22, 1991 (1978).) These polymers are easily soluble in ethanol or other simple solvents, and thus can be used to prepare matrices containing large unstable biological molecules that would be damaged by more aggressive solvents. The erosion rate can be tailored by adjusting the size of the ester group; the smaller the ester group, the more rapid being the erosion. Other polymers that could be used to make erosion-controlled systems include α-cyanoacrylates, such as methyl, ethyl, or higher alkyl cyanoacrylates. These polymers have been used as surgical adhesives, and microparticle formulations of methyl, ethyl and butyl cyanoacrylate are known.

The third mechanism whereby agents can be controllably released from the microparticles is by simple leaching. In this case, the polymer matrix may be non-biodegradable, or biodegradable after the agent supply is exhausted. The microparticles comprise a polymer in which the agent to be dispensed is insoluble, and dispersed within the polymer a sufficient loading of the active agent to create a network where the particles of agent touch. As the agent at the surface of the particle is leached away by the gingival fluid, an interpenetrating network of pores is created, and further delivery of the agent proceeds by dissolution of and flow of the agent out through these pores. In practice, even in nominally diffusion- or erosion-controlled monolithic dispersions, if the solid drug loading is greater than about 15 vol %, this pore-creation effect will occur, and at least a portion of the drug release will be in this fashion. This type of system is also useful for delivering growth factors or other large molecules that are insoluble and will not diffuse through the polymer matrix. Many polymer/agent combinations are possible, but the polymer chosen should be soluble in a solvent that will not attack the agent to be dispensed. In general, subject to this criterion, any of the polymers already listed above may be used. For example, as disclosed in U.S. Pat. No. 4,391,797, ethylene vinyl acetate has been used as a matrix for a variety of enzymes.

The size of the microparticles should be limited to between 10 and 500 microns. Very small particles with consistent properties are difficult to prepare and they may wash out of the periodontal pocket easily. Particles larger than 500 microns are too large to deliver with a standard syringe and needle and may be uncomfortable or irritating to the gingival membranes.

The carrier medium used to contain the microparticles must conform to several requirements. First it should be biocompatible, non-toxic and non-allergenic. Secondly it should have a low solubility but a high permeability for the drug in question. A low solubility is preferred to minimize leaching of the drug from the microparticle prior to use. Alternatively, the active agent contained in the microparticles may also be deliberately incorporated into the carrier medium. This will both prevent the loss of agent from the particles and provide an initial dose of the agent to the patient as soon as the system is in place. High permeability is required in order that the drug be well conducted from the microparticle to the mucous membranes. Thirdly the carrier medium should promote good adhesion of the microparticles in the periodontal pocket, and last it should have an appropriate viscosity for the intended use. The choice of medically acceptable carriers is very wide and can include amongst others, water, aqueous solutions, syrups, alcohols, glycerine, mineral oil, vegetable oils, synthetic mucilage-like substances such as polyvinyl alcohol, carboxymethylcellulose and so on. Further examples which may be mentioned are the water soluble polymers listed by Suzuki et al. in U.S. Pat. No. 4,569,837, col. 4, lines 9 through 21. Simple saline solutions and similar aqueous solutions can be used, but may be washed out of the periodontal pocket too quickly. A preferred alternative is one of the thicker, viscous media such as carboxymethylcellulose. In general, the more viscous the medium, the better it will adhere in the periodontal pocket; however highly viscous carriers may be difficult to insert with a syringe and needle and consequently may not spread through the pocket to any useful extent. An especially preferred form then is a thermally gelling polymer, such as those vehicles disclosed by Krezanowski in U.S. Pat. No. 4,188,373. The Pluronic® series of polyoxypropylene-polyoxyethylene copolymers, marketed by BASF Wyandotte, Parsippany, New Jersey, contains several suitable examples. These polymers are compatible with many commonly used pharmaceutical materials, and have been approved by the FDA for medical use. The Pluronic series can be obtained in a range of molecular weights and compositions; thus the carrier formulation may be tailored for optimum performance in the environment of the invention. Aqueous solutions of Pluronic F127 in the concentration range 20–40 wt % are free-flowing liquids at refrigerator or room temperature, but gel rapidly at 30° C. or above. These solutions are amenable to delivery by the syringe/needle method, but quickly take on the necessary viscosity for good adhesion and durability once resident within the periodontal pocket. Thus these solutions are particularly preferred in the context of the present invention. Optionally, a self-gelling preparation such as those disclosed by Caslavsky et al. in U.S. Pat. No. 4,563,351 could be used for the carrier medium.

The system of the invention is especially valuable for insertion into the periodontal pocket for treatment of a variety of symptoms associated with periodontal disease. However, the scope of the invention is also intended to embrace use of the invention to treat infection, pain, inflammation and so on associated with other oral problems. As non-limiting examples, the system could be used in the healthy sulcus to dispense prophylactic agents, in the socket to treat alveolitis following tooth extraction, and in lesions or wounds arising from surgery or other causes.

EXAMPLE 1

Polycarbonate was used to prepare microparticles by the solvent evaporation process. The drug used was tetracycline free base (TFB). The aqueous phase was saturated with TFB before starting a microparticle preparation run. In this way migration of the TFB into the aqueous phase during particle formation was minimized, and it was possible to encapsulate 70 to 100% of the TFB used. Known amounts of TFB and polycarbonate dissolved in methylene chloride were added to an aqueous phase containing polyvinyl alcohol (PVA) and 3 ppm n-octanol. The PVA is an emulsifier and the n-octanol and anti-foaming agent. The solution was stirred continuously, and air was passed over it. As the methylene chloride evaporated, the emulsion droplets solidified. The microparticles thus formed were separated from the aqueous solution, dried and sieved to obtain three size fractions; 50-110 microns, 110-210 microns and 210-500 microns. The in vitro drug release rate was measured by dispersing a known amount of microparticles in a volume of aqueous saline solution (0.9% NaCl). The dispersion was stirred and kept at a temperature of 37° C. Samples were periodically removed and diluted and their antibiotic concentration determined by UV spectrophotometry. The total tetracycline content of the microparticles was determined in a similar way by dissolving a known amount of microparticles and measuring the antibiotic concentration. The presence of the matrix polymer in the solution does not interfere with the UV measurements. A typical result is shown by the upper curve in FIG. 1. The initial release rate was high, then remained fairly steady until it tapered off at times in excess of 25 hours. Drug loadings between 18 and 35 wt % were used. Unexpectedly, the release curves for the three size fractions were closely bunched; thus it appears that, contrary to theoretical prediction, the microparticle size is relatively unimportant as far as the drug release kinetics are concerned.

These experiments showed that microparticles made of polycarbonate containing 18 to 35 wt % tetracycline and ranging in size from 50 to 500 microns were capable of delivering tetracycline in a sustained fashion for periods of about 25 hours. Since the periodontal pocket is small and its fluid exchange rate slow, the flow of gingival fluid in a single periodontal pocket being of the order of 10 microliters per hour, this in vitro release rate is estimated to correspond to an in vivo release period of the order of 10 to 20 days.

EXAMPLE 2

The method as described in Example 1 was used to prepare microparticles. Polysulfone was chosen as the matrix material; the drug used was TFB. A typical release curve is shown as the lower curve in FIG. 1. As can be seen the drug release rate was very slow, only a small fraction of the total drug loading having been released after 24 hours.

EXAMPLE 3

Figure 2:
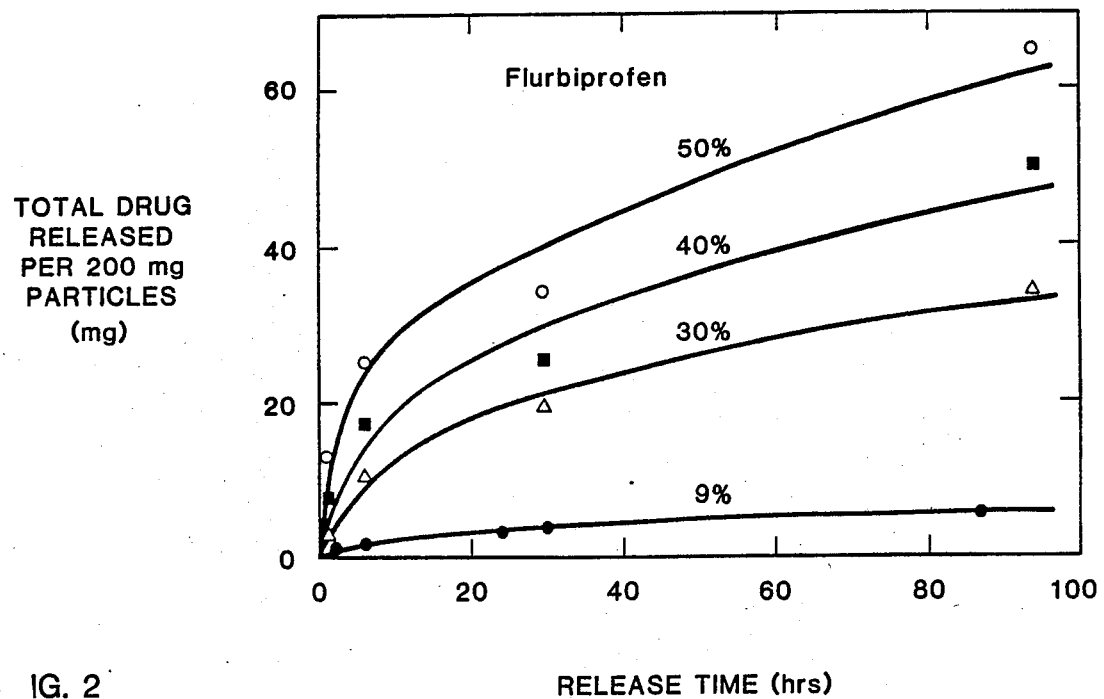
FIG. 2 is a graph of in vitro release of flurbiprofen from ethylcellulose particles.

A series of flurbiprofen microcapsules suitable for use in a periodontal formulation were prepared by the solvent evaporation method. Varying amounts of flurbiprofen were dissolved in ethylcellulose (medium ethoxy, viscosity 100 (Dow Chemical Co., Midland, MI) in methylene chloride solution. Fifteen ml of this solution were emulsified in 600 ml of aqueous 60 bloom gelatin stirred at 500 rpm. Two drops of octanol were added to eliminate foam. The methylene chloride was evaporated at 30° C. After 55 minutes the stirrer was shut off and the mixture was allowed to settle. The hollow capsules floating on the surface were decanted and the remaining capsules were collected on fine filter paper using a buchner funnel. The capsules were then placed in a foil dish in a dehymidifying cabinet. The drug release rates of the ethylcellulose capsules with varying drug contents were measured. These results are shown in FIG. 2. The flurbiprofen content of various batches of microcapsules is also shown on this figure. As shown, the microcapsule delivery rate can be varied over a wide range by varying the drug to polymer ratio in the microcapsules.

EXAMPLE 4

Figure 3:
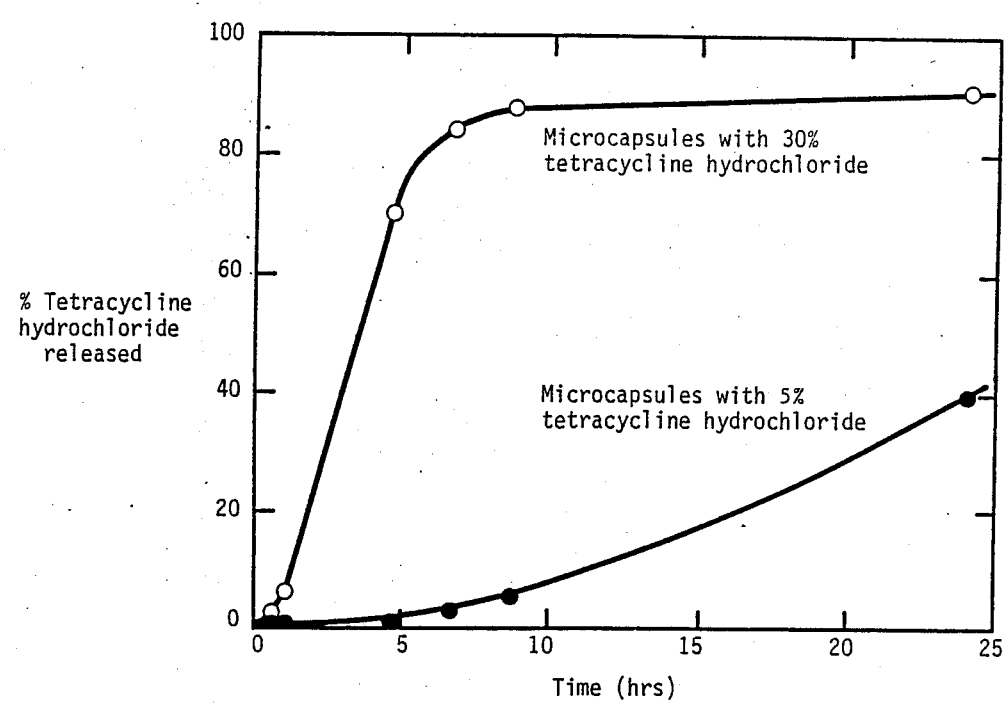
FIG. 3 is a graph of in vitro release of tetracycline hydrochloride from 50:50 poly(lactide-co-glycolide) microparticles.

Batches of biodegradable microparticles were prepared from poly(lactide-coglycolide) having lactic and glycolic moieties in equal proportions. The drug used was tetracycline hydrochloride (THC). The microparticles were sieved into size fractions ranging from 25 to 210 microns. Particles with drug loadings of 5 wt % and 30 wt % were prepared. Drug release into saline solution was measured as described in Example 1 above. Typical results obtained with particles of 25-210 micron diameter are shown by the two curves in FIG. 3.

EXAMPLES 5 TO 10

Preparation of Diffusion-Controlled Systems

EXAMPLE 5

Microparticles of poly(hydroxyethyl methacrylate) (HEMA) containing cephalosporin C Water-swellable microparticles are prepared by free-radical polymerization of 2-hydroxyethyl methacrylate with a difunctional vinyl crosslinking agent such as N,N'-methylene bisacrylamide. The permeability of the resulting hydrogel particles can be tailored to some extent by the degree of crosslinking. Typical proportions of monomer:crosslinker are 75:25. To encapsulate the antibiotic, the microparticles in the size fraction 250-500 microns are mixed into a saturated solution of the sodium salt of cephalosporin C in an aqueous solvent in a 1-liter flask. The contents of the flask are allowed to come to equilibrium, then the particles are removed, filtered, rinsed and vacuum or freeze dried. The drug is then trapped in the particles until they are placed in an aqueous carrier, where they will swell, thereby releasing the antibiotic by diffusion.

EXAMPLES 6 AND 7

Microparticles of poly(D,L-lactide) containing chlorhexidine or penicillins

The dihydrochloride salt of chlorhexidine is prepared by neutralizing the chlorhexidine base with hydrochloric acid. The polymer is prepared by melting a quantity of crystalline D,L-lactide in a 2-liter flask at a temperature of 125° C., adding a suitable catalyst, such as stannous octoate, and stirring the contents of the flask for several hours. The resulting high molecular weight polymer is used to make drug-loaded microparticles according to the solvent evaporation method of Example 1 as follows. An organic phase is prepared by suspending equal weights of the drug and polymer in methylene chloride. This organic phase is added to an aqueous phase containing about 5% of PVA as an emulsifier, and a few ppm n-octanol as anti-foaming agent. Stirring is continued for 2-4 hours, then the resulting microparticles are separated from the solution, briefly rinsed in deionized water, dried and sieved into size fractions.

The same procedure is used to prepare microparticles loaded with Penicillin G Benzathine or Penicillin V Potassium.

EXAMPLE 8

Alginic acid microparticles containing tibezonium iodide

The microparticle material is prepared by combining 1 g alginic acid, 1 g tibezonium iodide and 100 ml of saline and heating and stirring for up to 1 day until all the antiseptic is in suspension. A solution of 1.5 wt % calcium chloride in saline is placed in a 1-liter beaker. The microparticle solution is pumped through a nozzle with a diameter of 300 microns, and falls as droplets into the stirred calcium chloride solution. The thus formed particles are decanted 3 times with saline solution, and transferred to a smaller beaker, to which is added 100 ml of a 0.1% poly-L-lysine (MW 14,000) in saline solution. The poly-L-lysine acts as a crosslinking agent. The solution is stirred for 1-2 hours, then decanted. The microparticles are washed several times in saline and dried. Microparticles of this type will normally release the agent contained by diffusion in vitro over a period of up to 1 week, and degrade over a period of 3-6 weeks.

EXAMPLE 9

Alginate microparticles containing human growth factor TGF-B

The general procedure followed is the same as that in Example 8. The microparticle material is a suspension of 2% tissue growth factor TBF-B in saline added to a 1.5% solution of sodium alginate in saline. The droplets are deposited into calcium chloride as above. The crosslinking step is carried out in a 0.02% poly-L-lysine (MW 35,000) solution for 5 minutes. The microparticles are washed several times each in dilute solutions of calcium chloride, saline, and alginic acid, then freeze dried and stored in sealed vials until required.

EXAMPLE 10

Hydrogel particles containing fluoride

A copolymer of methyl methacrylate (MMA) and hydroxyethyl methacrylate (HEMA) is prepared by adding equal molar ratios of the two monomers to a 1-liter flask containing a 60:40 ethanol:water solution. The solution is purged with nitrogen, and a catalyst of 2:1 $Na_2S_2O_5:K_2S_2O_5$ is added. The flask is sealed and left for 10 days. The resulting polymer is washed several times in water, filtered, and dried under vacuum at 50° C. Drug-loaded films are then prepared as follows. Three grams of the copolymer is dissolved in 25 ml of 60:40 acetone:p-dixoane. One gram of micronized sodium fluoride is added to the solution, and the solution is cast as 200-micron thick films onto a glass plate. The film is left to dry, then ground in a laboratory mill to produce particles with an average diameter of 100-200 microns. The fluoride release from these particles can be tailored by varying the drug loading and the HEMA:MMA ratio.

Microparticles with a 50:50 monomer ratio will normally produce a useful fluoride release over a period of about 5 to 15 days.

EXAMPLES 11 TO 13

Preparation of Erosion-Controlled Systems

EXAMPLE 11

Microparticles of an n-hexyl half ester of a methyl vinyl ether/maleic anhydride copolymer containing ketorolac tromethamine A 2-liter flask is charged with 1-hexanol and methyl vinyl ether/maleic anhydride copolymer in a molar ratio of 11:1. The flask is heated to 145° C. and maintained at that temperature for 2-3 hours. The solution is then cooled to room temperature and precipitated in a large volume of 1:1 methanol:water. The precipitated polymer is dissolved in acetone and reprecipitated into 1:2 methanol:water. This step is repeated several times more, and the pure half-ester product is finally oven-dried for 2-3 days at 50° C.

The polymer is then used to prepare microparticles containing the potent anti-inflammatory and analgesic ketorolac. The ketorolac is used in the form of the tromethamine salt. The polymer is dissolved in a solvent consisting of 70:30 by weight 2-ethoxy ethyl acetate and isopropyl acetone. One part of micronized drug is added to every 10 parts of polymer. The dispersion is homogenized on a bottle roller for 2-4 hours. The solution is then poured into molds, left to air dry slowly for a week, then oven-dried at 35° C. for 1-2 days. The resulting films are then ground in a labortory mill to produce microparticles having an average diameter in the range 100-150 microns.

Microparticles of this type will normally degrade in vitro over a period of 4-5 days.

EXAMPLE 12

Microparticles of a polyanhydride containing lidocaine

Microparticles are prepared using the polyanhydride, poly(bis(p-carbxoyphenoxy)methane), which may be synthesized, for example, by the process described by A. Conix in *Macromolecular Synthesis*, Vol. 2, (J. R. Elliot, Ed.) pages 95-99, Wiley N.Y. (1966). Once prepared, the polymer is ground in a laboratory mill to obtain particles having an average diameter in the range 100-150 microns. The micronized drug is sieved to obtain a particle fraction with the same average diameter as the polymer. The drug and polymer particles are mixed together in the desired ratio, typically, for instance, 15 wt % drug, then compression molded by melt pressing at 20-50 Kpsi for about 10 minutes. The resulting film is then cooled to room temperature and reground to 100-150 micron particles. These are then melt pressed as above. The process is repeated three times more to produce particles with an evenly distributed anaesthetic loading.

Particles of this type are generally found to completely degrade in vitro over about a week or more.

EXAMPLE 13

Cyanoacrylate microparticles containing human epidermal growth factor EGF

Cyanoacrylate microparticles may be prepared by the interfacial polymerization method, by emulsifying an aqueous phase containing human epidermal growth factor EGF in an organic solvent mixture such as 5 vol % sorbitan trioleate in 1:4 chloroform:cyclohexane. A second equal volume of organic phase containing butyl 2-cyanoacrylate is added, and the interfacial polymerization reaction is allowed to proceed for 2-5 minutes. The reaction is carried out in a 1-liter flask maintained at 4° C. by an ice jacket, and stirred continuously. Another equal volume of organic solvent is then added to dilute the reactant and prevent further reaction. The microparticles are left to settle and the solvent is drawn off. The particles are washed in a solution of polysorbate, water and ethanol, then centrifuged in a buffer solution. Microparticles of this type normally degrade in vitro over a period of 1-2 days.

EXAMPLES 14 AND 15

Preparation of Leaching-Controlled System

Antibiotic-containing microparticles are made by adding 1 g of micronized Cefadroxil to 20 ml of a 10% solution of Elvax 40 ® (ethylene-vinyl acetate copolymer with 40 wt % vinyl acetate) in methylene chloride. The solution is stirred and then poured into glass molds and then dried under vacuum for 1-2 days. The resulting films are removed from the molds and ground to produce particles with an average diameter of 200-250 microns. In an aqueous environment, this type of microparticle releases the antibiotic by leaching.

The same general procedure can be used to prepare microparticles loaded with human tissue growth factors.

EXAMPLE 16

A Combined Diffusion/Erosion Controlled System

Microparticles containing 2 wt % epidermal growth factor EGF are prepared from poly(lactide-co-glycolide) having lactic and glycolic moieties in equal proportions. An aqueous solution containing the growth factor is added to a solution of the polymer in methylene chloride. The solution is stirred vigorously to form a water-in-oil emulsion. A non-solvent is added to precipitate the polymer onto the aqueous phase. The resulting droplet suspension is added to a large volume of non-solvent to harden the particles, which are then washed, sieved and dried under vacuum.

The growth factor is released from these microparticles by both diffusion and erosion. The initial release is by diffusion of growth factor that is relatively close to the surface of the particle. Release then slows until the particles begin to erode, and drug is released as the particles disintegrate. The release pattern is adjusted by varying the molecular weight of the polymer; low molecular weight polymers degrade faster than those with high molecular weights. The molecular weight can be conveniently characterized by the intrinsic viscosity of the polymer. For this example, a 50:50 copolymer should have an intrinsic viscosity of 0.4 dL/g to produce a uniform pattern of release by erosion and diffusion.

I claim:

1. A controlled drug delivery system for placement in a periodontal pocket, comprising:
   (a) a plurality of discrete microparticles, between 10 and 500 microns in diameter, comprising a drug and a polymer containing said drug, wherein when said microparticles are placed in an environment of use, said drug is released at a controlled rate by a combination of diffusion of said drug through said polymer and erosion of said polymer; and
   (b) a fluid suspending medium for said microparticles; said drug delivery system remaining active in the periodontal pocket for a period of between one and thirty days.

2. The drug delivery system of claim 1, wherein said drug is a prophylactic agent chosen from the group consisting of calcium and fluoride.

3. The drug delivery system of claim 1, wherein said drug is an antiseptic chosen from the group consisting of chlorhexidine and tibezonium iodide.

4. The drug delivery system of claim 1, wherein said drug is an antibiotic.

5. The drug delivery system of claim 4, wherein said antibiotic is chosen from the group consisting of aminoglycosides, macrolides, penicillins and cephalosporins.

6. The drug delivery system of claim 4, wherein said antibiotic is chosen from the group consisting of tetracycline and tetracycline hydrochloride.

7. The drug delivery system of claim 1, wherein said drug is a local anaesthetic.

8. The drug delivery system of claim 7, wherein said local anaesthetic is lidocaine or procaine.

9. The drug delivery system of claim 1, wherein said drug is an anti-inflammatory.

10. The drug delivery system of claim 9, wherein said anti-inflammatory is chosen from the group consisting of ketorolac, naproxen, diclofenac sodium and flurbiprofen.

11. The drug delivery system of claim 1, wherein said drug possesses activity against collagen-destructive enzymes.

12. The drug delivery system of claim 11, wherein said drug is chosen from the group consisting of tetracyclines and sanguinarine, its compounds and derivatives.

13. A method for controlled delivery of a drug to a cavity within the mouth, comprising inserting into said cavity the drug delivery system of claim 1.

14. The method of claim 13, wherein said cavity is a wound.

15. The method of claim 13, wherein said cavity is a socket created by tooth extraction.

16. The method of claim 13, wherein said cavity is a periodontal pocket.

17. The method of claim 13, wherein said cavity is a gingival sulcus.

18. A controlled drug delivery system for placement in a periodontal pocket, comprising:
   (a) a plurality of discrete microparticles, between 10 and 500 microns in diameter, comprising a drug and a polymer containing said drug, said drug being essentially insoluble in said polymer, wherein when said microparticles are placed in an environment of use, said drug is released at a controlled rate by erosion of said polymer; and
   (b) a fluid suspending medium for said microparticles; said drug delivery system remaining active in the periodontal pocket for a period of between one and thirty days.

19. The drug delivery system of claim 18, wherein said drug is a prophylactic agent chosen from the group consisting of calcium and fluoride.

20. The drug delivery system of claim 18, wherein said drug is an antiseptic chosen from the group consisting of chlorhexidine and tibezonium iodide.

21. The drug delivery system of claim 18, wherein said drug is an antibiotic.

22. The drug delivery system of claim 21, wherein said antibiotic is chosen from the group consisting of aminoglycosides, macrolides, penicillins and cephalosporins.

23. The drug delivery system of claim 21, wherein said antibiotic is chosen from the group consisting of tetracycline and tetracycline hydrochloride.

24. The drug delivery system of claim 18, wherein said drug is a local anaesthetic.

25. The drug delivery system of claim 24, wherein said local anaesthetic is lidocaine or procaine.

26. The drug delivery system of claim 18, wherein said drug is an anti-inflammatory.

27. The drug delivery system of claim 26, wherein said anti-inflammatory is chosen from the group consisting of ketorolac, naproxen, diclofenac sodium and flurbiprofen.

28. The drug delivery system of claim 18, wherein said drug possesses activity against collagen-destructive enzymes.

29. The drug delivery system of claim 28, wherein said drug is chosen from the group consisting of tetracyclines and sanguinarine, its compounds and derivatives.

30. The drug delivery system of claim 18, wherein said drug is a tissue growth factor.

31. The drug delivery system of claim 30, wherein said tissue growth factor is chosen from the group consisting of epidermal growth factors (EGF), human platelet derived TGF-B, endothelial cell growth factors (ECGF), thymocyte-activating factors (TAF), platelet derived growth factors (PDGF), fibroblast growth factor (FGF), fibronectin and laminin.

32. A method for controlled delivery of a drug to a cavity within the mouth, comprising inserting into said cavity the drug delivery system of claim 18.

33. A controlled drug delivery system for placement in a periodontal pocket, comprising:
   (a) a plurality of discrete microparticles, between 10 and 500 microns in diameter, comprising at least 15 vol % drug dispersed in a polymer, said drug being essentially insoluble in said polymer, wherein when said microparticles are placed in an environment of use, said drug is released at a controlled rate by leaching of said drug from said polymer; and
   (b) a fluid suspending medium for said microparticles; said drug delivery system remaining active in the periodontal pocket for a period of between one and thirty days.

34. The drug delivery system of claim 33, wherein said drug is a prophylactic agent chosen from the group consisting of calcium and fluoride.

35. The drug delivery system of claim 33, wherein said drug is an antiseptic chosen from the group consisting of chlorhexidine and tibezonium iodide.

36. The drug delivery system of claim 33, wherein said drug is an antibiotic.

37. The drug delivery system of claim 36, wherein said antibiotic is chosen from the group consisting of aminoglycosides, macrolides, penicillins and cephalosporins.

38. The drug delivery system of claim 36, wherein said antibiotic is chosen from the group consisting of tetracycline and tetracycline hydrochloride.

39. The drug delivery system of claim 33, wherein said drug is a local anaesthetic.

40. The drug delivery system of claim 33, wherein said local anaesthetic is lidocaine or procaine.

41. The drug delivery system of claim 33, wherein said drug is an anti-inflammatory.

42. The drug delivery system of claim 41, wherein said anti-inflammatory is chosen from the group consisting of ketorolac, naproxen, diclofenac sodium and flurbiprofen.

43. The drug delivery system of claim 33, wherein said drug possesses activity against collagen-destructive enzymes.

44. The drug delivery system of claim 43, wherein said drug is chosen from the group consisting of tetracyclines and sanguinarine, its compounds and derivatives.

45. The drug delivery system of claim 33, wherein said drug is a tissue growth factor.

46. The drug delivery system of claim 45, wherein said tissue growth factor is chosen from the group consisting of epidermal growth factors (EGF), human platelet derived TGF-B, endothelial cell growth factors (ECGF), thymocyte-activating factors (TAF), platelet derived growth factors (PDGF), fibroblast growth factor (FGF), fibronectin and laminin.

47. A method for controlled delivery of a drug to a cavity within the mouth, comprising inserting into said cavity the drug delivery system of claim 33.

* * * * *